United States Patent [19]

Hedberg

[11] Patent Number: 5,395,395
[45] Date of Patent: Mar. 7, 1995

[54] METHOD AND APPARATUS FOR INCREASING THE ENERGY OUTPUT FROM A BANK OF CAPACITORS

[75] Inventor: Sven-Erik Hedberg, Kungsaengen, Sweden

[73] Assignee: Siemens Aktiengesellschaft, Munich, Germany

[21] Appl. No.: 115,554

[22] Filed: Sep. 3, 1993

[30] Foreign Application Priority Data

Sep. 16, 1992 [SE] Sweden .................. 9202666

[51] Int. Cl.⁶ ............................ A61N 1/39
[52] U.S. Cl. .......................... 607/7; 607/5
[58] Field of Search .................. 607/5, 7, 4

[56] References Cited

U.S. PATENT DOCUMENTS 5,199,429  4/1993  Kroll et al. ............... 607/5

FOREIGN PATENT DOCUMENTS 0272021  7/1964  Australia .................. 607/5
0445800  3/1991  European Pat. Off. .
 976994  6/1962  United Kingdom .
1387115  3/1975  United Kingdom .

Primary Examiner—William E. Kamm
Assistant Examiner—Kennedy J. Schaetzle
Attorney, Agent, or Firm—Hill, Steadman & Simpson

[57] ABSTRACT

In a method for increasing the energy output from a number of charged capacitors each of the capacitors is discharged, one after another, through a load. The capacitors are then coupled in series in successive, different combination, each of which includes a part or all of the capacitors. These combinations are and being discharged, one after another, through the load. An apparatus for increasing the energy output from a number of charged capacitors includes comprises a charging circuit, arranged to control the charging of the capacitors, and a controllable switching device, arranged to first connect each of the capacitors to a load for discharge of the capacitors, on after another. The switching device then couples the capacitors in series in successive, different combinations, each of which includes a part or all of the capacitors, and connects the respective combinations to the load for discharge of the series couplings, on after another.

17 Claims, 1 Drawing Sheet

METHOD AND APPARATUS FOR INCREASING THE ENERGY OUTPUT FROM A BANK OF CAPACITORS

BACKGROUND OF THE INVENTION

1. Field of the Invention

The present invention relates to a method and an apparatus for increasing the energy output from a plurality of charged capacitors.

2. Description of the Prior Art

The generation of pulses with an amplitude equal to twice the voltage of a charging battery when two capacitors connected in parallel are charged, the capacitors thereafter being connected in series to emit the pulse, is known. This technique has been used in, e.g., pacemakers.

SUMMARY OF THE INVENTION

An object of the present invention is to enable the largest possible output of energy, stored in a plurality of capacitors, during the emission of a pulse which more closely resembles a square pulse than a pulse discharged from a single capacitor having the same capacitance as the sum of the capacitances of the plurality of capacitors.

The above object is achieved in accordance with the principles of the present invention in a method wherein each one of a number of charged capacitors is discharged, one after another, through a load. The capacitors are then coupled in series in successive, different combinations, each combination including a part or all of the total number of capacitors. These combinations are discharged, one after another, through the load.

The above object is achieved in an apparatus wherein a number of capacitors are charged by a charging circuit, and a controllable switching device is operated to connect each of the capacitors individually to a load for discharge of the individual capacitors, one after another. The switching device then couples the capacitors in series and successive, different combinations, each combination including a part or all of the total number of capacitors. The switching device connects the respective combinations to the load for discharge of the series couplings, one after another.

Each capacitor in the plurality of capacitors has a relatively brief time constant, so the corresponding discharge pulses would normally abate with unacceptable rapidity. However, according to the invention "new" capacitors are connected, one after another, and two or more capacitors in different series combinations are successively connected in series for discharge until each capacitor has been used individually in this way. This results in the voltage of the composite discharge pulse emitted this way being maintained, and substantially square pulse is achieved.

The capacitors can be connected in parallel or in series for the best possible output of energy.

According to further embodiments of the method of the invention, each capacitor discharge is stopped when the voltage across the load drops to a predesignated level, preferably a constant level, for all the discharges. Alternatively, each capacitor discharge can be allowed to continue for a predesignated period of time, preferably a constant period of time for all the discharges.

The apparatus according to the invention includes charging circuitry for charging the capacitors to the desired voltage and a controllable switching device which connects the capacitors in different discharge configurations.

The switching device can be controlled with varying degrees of complexity, and the charging circuitry and the switching device are controlled by a control unit, preferably a microprocessor, according to one embodiment of the invention. The control unit can determine (calculate) the most advantageous combination of capacitors for the discharge and sets the switching device accordingly, or the control unit can select a sequence among previously programmed capacitor coupling sequences which proved to be effective.

In another embodiment of the apparatus of the invention, a measurement circuit is provided to measure the voltage across the capacitors and the series connections of the capacitors during the discharges, and stops the discharges when the measured voltage drops to a designated level. The measurement circuit preferably employs A/D converters which send the measured voltage values to the control unit after each sub-discharge of the ensuing output pulse. If an unfavorable voltage is measured across any capacitor, this capacitor can be excluded from the coupling configuration or possibly have its polarity reversed.

DESCRIPTION OF THE PREFERRED EMBODIMENTS

Figure 1:
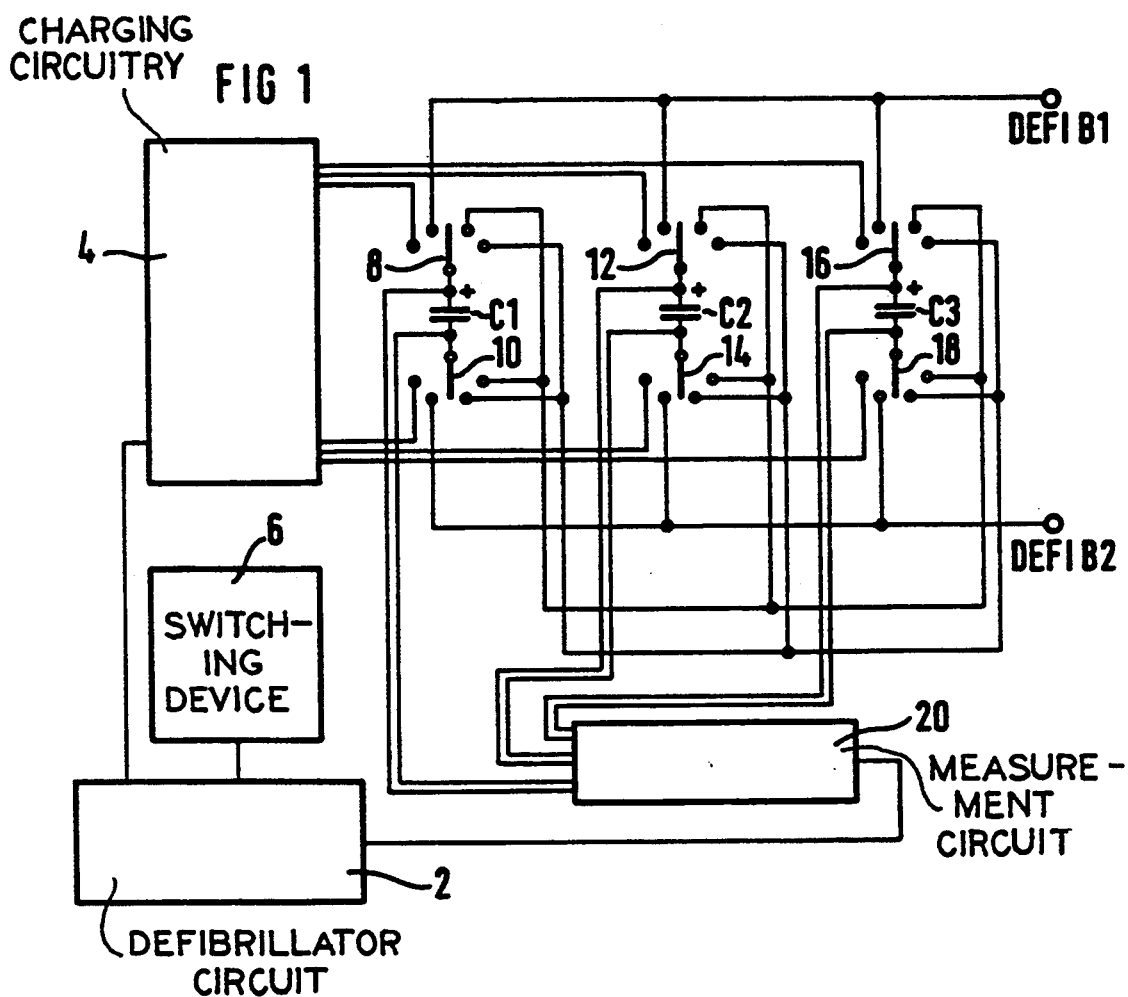
FIG. 1 is a schematic block diagram of an apparatus for increasing the energy output from a bank of capacitors, constructed in accordance with the principles of the present invention, in the context of a heart defibrillator.

The heart defibrillator according to FIG. 1 includes a defibrillator circuit 2 containing a control unit in the form of a microprocessor which, via its ports, controls charging circuitry 4 for the capacitors C1, C2 and C3 and also controls a switching device 6.

Before the discharge operation for generating a defibrillation pulse starts, the capacitors C1, C2 and C3 are charged from a battery by means of the charging circuitry 4.

The intercoupling of the capacitors C1, C2 and C3 in different configurations during the discharge operation is controlled by the microprocessor in the defibrillation circuit 2.

Switches 8, 10, 12, 14, 16 and 18 for intercoupling the capacitors C1, C2 and C3 in different configurations are controlled by the switching device 6. The connections between the switching device 6 and the switches 8, 10, 12, 14, 16 and 18, however, are easily devisable by those skilled in the art, and are therefore omitted for drawing clarity. The switchings in connection with the discharge operation will be explained below in greater detail in conjunction with FIG. 2.

The voltage across each capacitor C1, C2 and C3 is measured by a measurement circuit 20 after each discharge phase. The measurement circuit 20 can also continuously measure the voltage across one or more capacitors during the discharge operation in order to stop the prevailing discharge, via the microprocessor in the defibrillation circuit 2, when the voltage across the capacitor or capacitors drops to a designated level. The measurement circuit 20 can contain A/D converters which deliver values for the measured voltage to the microprocessor of the defibrillation circuit 2, representing the capacitor voltage measured.

If a voltage, unfavorable in a given context, occurs across any capacitor, this capacitor can be left out in the coupling configuration. For example, the polarity of a given capacitor can be reversed. If, two capacitors charged to different voltages are connected in series and the same current flows in the circuit, the discharge will continue and current will be impelled by the capacitor with the higher voltage, so the polarity of the capacitor charged to the lower voltage is reversed. Thus, such a capacitor with reversed polarity will be bypassed in the envisaged coupling configuration or have its polarity reversed in the apparatus according to the invention.

Figure 2:
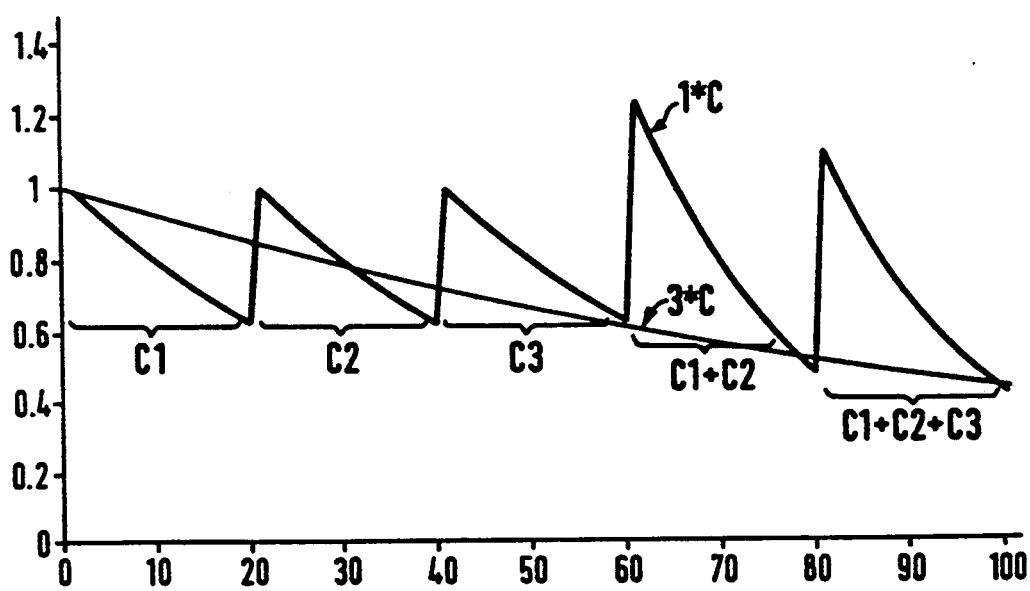
FIG. 2 shows an example of the curve of an output pulse from the circuit shown in FIG. 1.

FIG. 2 shows the time curve for the output voltage across the output contacts DEFIB1 and DEFIB2. In this example, it is assumed that the capacitors C1, C2 and C3 are of equal size. The time and voltage axes are subdivided in time and voltage units appropriate to the drawing.

The capacitors C1, C2 and C3 are connected in parallel to the charging circuit 4 before any discharge operation, so as to charge the capacitors C1, C2 and C3 to the desired voltages. The discharge operation then begins, the switches 8, 10, 12, 14, 16 and 18 being initially in the positions shown in FIG. 1 in which none of the switches 8, 10, 12, 14, 16 and 18 conducts.

In the first three phases of the discharge operation, the capacitors C1, C2 and C3 are coupled, one after another, to the contacts DEFIB1 and DEFIB2 for discharging each of the capacitors C1, C2 and C3 for a given period of time, i.e., 20 time units in FIG. 2, the voltages of the capacitors C1, C2 and C3 then dropping to the same level. The capacitors C1 and C2 are then connected in series, and this series coupling is connected to the output contacts DEFIB1 and DEFIB2 for discharging C1 and C2, connected in series, for an additional 20 time units, from 60 time units to 80 time units in FIG. 2.

Capacitor C3 is subsequently connected to the serially coupled C1 and C2, so the series coupling formed by all three capacitors C1, C2 and C3 is coupled to the output contacts DEFIB1 and DEFIB2 for discharge for an additional 20 time units, from 80 time units to 100 time units.

For comparison, the output pulse which would be supplied by a single capacitor with the same capacitance as the three capacitors, C1, C2 and C3 jointly is illustrated in FIG. 2. As shown in FIG. 2, an output pulse is achieved with the apparatus according to the invention which more closely resembles a square pulse than the discharge pulse from this single capacitor.

With the invention, a biphasic pulse can also be achieved through phase reversal of the defibrillation pulse at a given time. In the example shown in FIG. 2, the phase of the pulse could therefore be reversed at the time 60 time units when the discharge of capacitors C1 and C2, connected in series, begins.

The way in which the switches 8, 10, 12, 14, 16 and 18 are to be set at different phases of the discharge operation, so the course shown in FIG. 2 is achieved, is apparent from FIG. 1.

FIG. 2 shows that each capacitor has a rather short time constant, so every individual capacitor would emit a pulse which decayed far too rapidly, but since new capacitors are coupled, one after another, and two or more capacitors connected in series are then discharged, the output voltage rises, and the capacitors can be discharged to a greater degree.

When the apparatus contains more than two capacitors, the intercoupling of these capacitors during the discharge operation can either be in parallel or series, so the best possible utilization of energy is achieved. As noted above, the voltage across a capacitor may be reversed. The capacitor polarity can then be reversed or the capacitor could simply not be connected.

With appropriate programming of the microprocessor in the defibrillation circuit 2, the microprocessor can calculate the most favorable capacitor configuration or select among programmed coupling sequences previously found to be effective.

One example of the apparatus according to the invention with three capacitors of equal size was described above. Both the number of capacitors and their size are clearly optional in the apparatus according to the invention.

The apparatus is described above using an example applied to a heart defibrillator, however, the apparatus according to the invention can also be used for many other kinds of applications for which an increase in the energy output of capacitors and the best possible utilization of stored energy are desired.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for increasing the energy output from a plurality of charged capacitors comprising the steps of:
    discharging each of said capacitors in said plurality of capacitors, one after another, individually through a load;
    successively coupling said capacitors in said plurality of capacitors in series in different combinations, each combination including a part or all of said plurality of capacitors; and
    discharging each of said different combinations, one after another, through said load.

2. A method as claimed in claim 1 wherein the steps of coupling said capacitors in different combinations and discharging said different combinations are further defined by the steps of:
    connecting a number, less than said plurality, of said capacitors in series after each of said capacitors has been individually discharged;
    discharging the series connection of said number of capacitors through said load;
    connecting one further capacitor of said plurality of capacitors to the existing number of capacitors connected in series to obtain a new series connection;
    discharging said new series connection through said load; and
    continuously adding one further capacitor to the previously existing number of capacitors connected in series and discharging each new series connection of capacitors through said load until all of said capacitors in said plurality of capacitors are connected in series, and discharging said series connection of said plurality of capacitors through said load.

3. A method as claimed in claim 1 comprising the additional step of:

stopping each discharge of an individual capacitor or a combination of capacitors when a voltage across said load drops to a predetermined level.

4. A method as claimed in claim 1 comprising the additional step of:
stopping each discharge of an individual capacitor or a combination of capacitors when a voltage across said load drops to a designated level which is a constant level for all of said discharges.

5. A method as claimed in claim 1 comprising the additional step of:
continuing each discharge of an individual capacitor or a combination of capacitors for a designated period of time.

6. A method as claimed in claim 1 comprising the additional step of:
continuing each discharge of an individual capacitor or a combination of capacitors for a designated period of time which is constant for all of said discharges.

7. An apparatus for increasing the energy output from a plurality of charged capacitors comprising:
a plurality of capacitors;
means for charging said capacitors;
controllable switching means for discharging said capacitors by first connecting each of said capacitors in said plurality of capacitors to a load for individually discharging said capacitors through said load, one after another, and for subsequently coupling said capacitors in series in successively different combinations, each combination including a part or all of said plurality of capacitors, and for connecting said different combinations to said load for discharging said different combinations through said load one after another.

8. An apparatus as claimed in claim 7 wherein said switching means comprises means for coupling a number, less than said plurality, of capacitors in said plurality of capacitors in series and for connecting said number of capacitors coupled in series to said load for discharge through said load after each of the capacitors has been individually connected to said load for discharge, and for subsequently coupling a further capacitor in said plurality of capacitors in series to the existing number of capacitors coupled in series to obtain a new series coupling, and connecting said new series coupling to said load for discharging said new series coupling through said load, and for continuing to add a further capacitor to the existing number of capacitors coupled in series until all capacitors in said plurality of capacitors have been coupled in series and each number of capacitors is discharged through said load.

9. An apparatus as claimed in claim 8 wherein the initial number of capacitors connected in series comprises two capacitors in said plurality of capacitors.

10. An apparatus as claimed in claim 7 further comprising measurement means for measuring the voltage across each of said capacitors.

11. An apparatus as claimed in claim 5 further comprising timer means for controlling said switching means for causing each discharge of a capacitor or a combination of capacitors to last for a designated period of time.

12. An apparatus as claimed in claim 5 further comprising a microprocessor connected for operating said charging means and said switching means.

13. An apparatus as claimed in claim 12 wherein said microprocessor comprises means for controlling said switching means according to a selected one of a plurality of pre-programmed coupling sequences for said capacitors.

14. An apparatus as claimed in claim 13 further comprising:
measurement means for measuring the voltage across each of said capacitors in analog form;
an analog-to-digital converter for converting said analog form of said voltages into digital form for delivery to said microprocessor.

15. An apparatus as claimed in claim 7 wherein said charging means comprises means for coupling said capacitors in parallel to a charging source.

16. An apparatus as claimed in claim 17 wherein each of said capacitors has the same capacitance.

17. An apparatus as claimed in claim 7 further comprising a defibrillation circuit containing said controllable switching means, and wherein said controllable switching means comprises means for controlling discharge of said plurality of capacitors individually and in said combinations for forming a heart defibrillation pulse.

* * * * *